United States Patent [19]

Hinnenkamp et al.

[11] Patent Number: 4,724,275

[45] Date of Patent: Feb. 9, 1988

[54] CRYSTALLINE ALUMINOSILICATES AND THEIR USE IN THE CONVERSION OF METHANOL TO LOW MOLECULAR WEIGHT HYDROCARBONS

[75] Inventors: James A. Hinnenkamp, Cincinnati, Ohio; John A. Scheben, Erlanger, Ky.; Vernon V. Walatka, Cincinnati, Ohio

[73] Assignee: National Distillers and Chemical Corporation, New York, N.Y.

[21] Appl. No.: 750,457

[22] Filed: Jul. 1, 1985

[51] Int. Cl.$^4$ .......................... C07C 1/00; C07C 5/13; C07C 27/06

[52] U.S. Cl. .................... 585/733; 585/277; 585/739; 518/715; 502/74

[58] Field of Search .................. 502/74; 518/715; 585/277, 739, 733; 423/328, 328 T, 329

[56] References Cited

U.S. PATENT DOCUMENTS

| | | | |
|---|---|---|---|
| 3,600,332 | 8/1971 | Huntel | 423/328 |
| 4,093,643 | 6/1978 | Vannice et al. | 518/715 |
| 4,157,338 | 6/1979 | Haas et al. | 502/74 |
| 4,299,686 | 11/1981 | Kuehl | 423/328 |
| 4,344,868 | 8/1982 | Chang et al. | 502/74 |
| 4,471,150 | 9/1984 | Wu | 585/640 |
| 4,517,306 | 5/1985 | Buss | 502/74 |
| 4,539,304 | 9/1985 | Field | 502/85 |
| 4,539,305 | 9/1985 | Wilson et al. | 502/85 |
| 4,547,618 | 10/1985 | Forbus | 585/660 |

FOREIGN PATENT DOCUMENTS

| | | | |
|---|---|---|---|
| 90442 | 10/1983 | European Pat. Off. | 585/739 |
| 978261 | 12/1964 | United Kingdom | 502/74 |
| 2099716 | 11/1982 | United Kingdom | 502/74 |

Primary Examiner—Gary P. Straub
Attorney, Agent, or Firm—Kenneth D. Tremain

[57] ABSTRACT

Crystalline Group VIII metal aluminosilicate compositions which are prepared by exchanging or impregnating a Group VIII metal onto an aluminosilicate. Conversion of methanol in the presence of a hydrogen co-feed to low molecular hydrocarbons employing these aluminosilicates as catalysts is also disclosed.

4 Claims, No Drawings

CRYSTALLINE ALUMINOSILICATES AND THEIR USE IN THE CONVERSION OF METHANOL TO LOW MOLECULAR WEIGHT HYDROCARBONS

BACKGROUND OF THE INVENTION

1. Field of the Invention

The present invention relates to aluminosilicate compositions and the catalytic conversion of methanol in the presence of a hydrogen cofeed to low molecular weight hydrocarbons utilizing these compositions.

2. Discussion of the Prior Art

Zeolite materials, both natural and synthetic, are known to have catalytic capability for various types of reactions, especially hydrocarbon conversions. The well known crystalline aluminosilicate zeolites are commonly referred to as "molecular sieves" and are characterized by their highly ordered crystalline structure and uniformly dimensioned pores, and are distinguishable from each other on the basis of composition, crystal structure, adsorption properties and the like. The term "molecular sieves" is derived from the ability of the zeolite materials to selectively adsorb molecules on the basis of their size and form.

The processes for producing such crystalline synthetic zeolite are well known in the art. A family of crystalline aluminosilicate zeolites, designated ZSM-5, is disclosed in U.S Pat. No. 3,702,886, said patent being herein incorporated by reference.

U S. Pat. No. 3,941,871 relates to novel crystalline metal organosilicates which are essentially free of Group IIIA metals, eg., aluminum and/or gallium. This patent is herein incorporated by reference. It is noted therein that the amount of alumina present in the known zeolites appears directly related to the acidity characteristics of the resultant product and that a low alumina content has been recognized as being advantageous in attaining a low degree of acidity which in many catalytic reactions is translated into low coke making properties and low aging rates. A typical procedure for making the organosilicates is to react a mixture containing a tetraalkylammonium compound, sodium hydroxide, an oxide of a metal other than a metal of Group IIIA, and oxide of silicon, and water until crystals of said metal organosilicates are formed. It is also noted in the patent that the family of crystalline metal organosilicates have a definite X-ray diffraction pattern which is similar to that of the ZSM-5 zeolites. Minor amounts of alumina are contemplated in the patent and are attributable primarily to the presence of aluminum impurities in the reactants and/or equipment employed.

U.S. Pat. No. 3,884,835 discloses crystalline silica compositions. The crystalline silica materials may also contain a metal promoter which may be selected from Group IIIA, Group VB or Group VIB elements. Boron is disclosed as one of the metal promoters.

U.S. Pat. No. 4,088,605 is directed to the synthesis of a zeolite, such as ZSM-5, which contains an outer shell free from aluminum. The patent states at column 10, the paragraph beginning at line 20, that to produce the outer aluminum-free shell, it is also essential that the reactive aluminum be removed from the reaction mixture. It is therefore necessary, as noted therein, to process the zeolite and to replace the crystallization medium with an aluminum-free mixture to obtain crystallization of $SiO_2$ on the surface of the zeolite which can be accomplished by a total replacement of the reaction mixture or by complexing from the original reaction mixture any remaining aluminum ion with reagents such as gluconic acid or ethylenediaminotetraacetic acid (EDTA).

Crystalline borosilicate compositions are disclosed in German Offenlegungschrift No. 2,746,790. This application relates specifically to borosilicates which are prepared using the usual procedures for making the aluminosilicate zeolites. It is noted therein, that in instances where a deliberate effort is made to eliminate aluminum from the borosilicate crystal structure because of its adverse influence on particular conversion processes, the molar ratios of $SiO_2/Al_2O_3$ can easily exceed 2000-3000 and that this ratio is generally only limited by the availability of aluminum-free raw materials.

German Offenlegungschrift No. 2,848,849 relates to crystalline aluminosilicates of the ZSM-5 zeolite series. These particular zeolites have a silica to alumina mole ratio greater than 20 and are prepared from a reaction mixture containing a source of silica, alumina, a quaternary alkyl ammonium compound and a metal compound including such Group VIII metals as ruthenium, palladium and platinum. In Example 2, the crystalline aluminosilicate is prepared from a reaction mixture containing $RuCl_3$ and in Example 3, the reaction mixture contains $H_2PtCl_6 \cdot nH_2O$.

U.S. Pat. No. 4,468,474 discloses hydrogen activated catalyst compositions comprising iron, silicon and carbon that selectively convert gaseous mixtures to $C_2$–$C_6$ alkenes. It is further noted that the catalysts maintained their activity and high selectivity over a long period and that regeneration of partially deactivated catalysts can be accomplished by treatment with hydrogen at elevated temperature.

U.S. Pat. No. 4,052,472 discloses the conversion of methanol and/or methyl ethers to a mixture of hydrocarbons including polyalkylated aromatic hydrocarbons. The catalysts utilized in this process are crystalline aluminosilicate type zeolites, e.g. mordenites that have a silica to alumina ratio greater than about 15.

U.S. Pat. No. 4,100,219 discloses a catalyst which can be utilized in the production of $C_2$–$C_3$ olefins i.e. ethylene and propylene by selectively converting lower monohydric alcohols and their ethers. The catalysts are crystalline aluminosilicates having a silica to alumina ratio of at least 12 and having added amphorous silica in the internal structure of the zeolite.

U.S. Pat. No. 4,083,888 discloses the catalytic conversion of a methanol feed in the presence of a substantially anhydrous diluent. The catalyst utilized in the process is exemplified by ZSM-5 or other crystalline aluminosilicate zeolites.

A recent article entitled, "Hydrocarbons from Methanol" by Clarence D. Chang, Catal. Rev.—Sci. Eng., 25(1), 1-118 (1983) describes incorporating Group VIII metals into Y zeolites to control coke formation. These efforts were unsuccessful and the methanol feed decomposed to CO and $H_2$.

While the art has provided zeolitic catalysts having a wide variety of catalytic and adsorbtive properties, the need still exists for crystalline materials having different and/or enhanced catalytic properties. For example, an important use for a catalytic material is the conversion of methanol in the presence of a hydrogen cofeed to low molecular weight hydrocarbons. Further, many hydrocarbon conversion processes are performed employing zeolites, e.g. alkylation, oligomerization and isomerization. As is well-known in the art, it is important to maximize selectivity for a desired product.

Accordingly, it is an object of this invention to provide crystalline aluminosilicate compositions having different and enhanced catalytic properties.

Another object of this invention is to provide an improved method for the conversion of oxygenated compounds to selected end products.

A further object of this invention is to provide an improved method for the conversion of methanol in the presence of a hydrogen cofeed to low molecular weight hydrocarbons utilizing aluminosilicate compositions.

The achievement of these and other objects will be apparent from the following description of the subject invention.

SUMMARY OF THE INVENTION

These and other objects are achieved by incorporating a Group VIII metal onto the aluminosilicates of the present invention. Briefly, this invention relates to incorporating a Group VIII metal onto an aluminosilicate and the use of these compositions to convert methanol in the presence of a hydrogen cofeed to low molecular weight hydrocarbons, preferably $C_2$ to $C_4$ hydrocarbons. Consequently, when the aluminosilicates are used in accordance with the present invention in the conversion of methanol in the presence of a hydrogen cofeed to low molecular weight hydrocarbons, the aluminosilicates exhibit high catalytic activity in the conversion of methanol in the presence of a hydrogen cofeed to low molecular weight hydrocarbons with high selectivity for $C_2$–$C_4$ hydrocarbons. These properties are contrary to the results expected from this type of crystalline zeolite composition.

The compositions of this invention are prepared by a method which comprises:

(a) contacting a crystalline aluminosilicate with a Group VIII metal salt solution to incorporate said metal onto said crystalline aluminosilicate;

(b) calcining the Group VIII aluminosilicate in air at a temperature of about 300° C. to about 600° C. for at least 4 hours; and (c) heating the calcined Group VIII aluminosilicate in the presence of hydrogen from ambient temperature to an elevated temperature of about 300° C. to about 500° C. at a rate of temperature increase of about 0.5 to about 2.0° C. per minute.

In another embodiment, this invention relates to aluminosilicate compositions that are prepared by the method described above.

Still another embodiment of this invention relates to a method for the conversion of methanol comprising:

contacting methanol in the presence of a hydrogen cofeed with a catalytically effective amount of the aluminosilicate compositions described above under conversion conditions effective to provide $C_2$–$C_4$ hydrocarbons at a selectivity of at least 50%.

DETAILED DESCRIPTION OF THE INVENTION

This invention relates to a method of preparing aluminosilicate based catalysts, and their use in the catalytic conversion of methanol in the presence of a hydrogen cofeed to low molecular weight hydrocarbons, with high selectivity for $C_2$–$C_4$ hydrocarbons.

Zeolitic materials, both natural and synthetic, in naturally occurring and modified forms have been demonstrated as having catalytic capabilities for hydrocarbons conversion. Such zeolitic materials are ordered crystalline aluminosilicates having definite crystalline structures within which there are passages, pores, or cavities of definite ranges of size. Since the dimensions of these pores are such as to accept for adsorption molecules of certain dimensions while rejecting those of larger dimension, these materials have been referred to as "molecular sieves" and utilized in many ways taking advantage of these properties.

The aluminosilicates of this invention may be prepared by incorporating Group VIII metals onto various known zeolites. Palladium, ruthenium and palladium-platinum-manganese are the preferred species because of the improved catalyst stability they provide. The incorporation of either metal may be achieved by ion-exchange or impregnation.

Ion-exchange techniques known to those in the art, may be utilized. For example, typical ion-exchange techniques include contacting the aluminosilicates with a salt solution of the desired replacing cation or cations. Although, a wide variety of salts can be employed, particular preference is given to chlorides, nitrates and sulfates.

Alternatively, the aluminosilicates may be impregnated with palladium, platinum, ruthenium or palladium-manganese by addition of an ammonia solution or by the addition of an aqueous solution of an appropriate palladium, platinum, ruthenium or palladium-manganese salt. The ammonia solvent which is used may be liquid ammonia or aqueous ammonia containing greater than 50 weight percent ammonia. Prior to impregnation with the solution, the aluminosilicate should, if necessary be calcined at about 300° C. to about 600° C. for at least 4 hours in air or an inert atmosphere to drive off any organic cations which would tend to block the pore structure of the aluminosilicate.

Addition of the ammonia to a Group VIII metal compound dissolves the Group VIII metal ions and the resulting solution permeates and impregnates the Group VIII metal onto the aluminosilicate. After impregnation, the aluminosilicate is dried, generally under mild conditions, to drive off the solvent and fix the Group VIII metal on the aluminosilicate. Temperatures of up to about 200° C., preferably about 110° C. to about 130° C. are suitable for this purpose.

The percent by weight of Group VIII metal that is ion-exchanged or impregnated onto the aluminosilicate significantly affects the catalytic activity and selectively for $C_{2-4}$ hydrocarbons in the conversion of methanol in the presence of the hydrogen cofeed. The lower the percent by weight of Group VIII metal present in the aluminosilicate, generally the lower the catalytic activity for the conversion of methanol to $C_2$–$C_4$ hydrocarbons. The percent by weight of palladium or platinum present in the aluminosilicate should be about 0.1 weight % to about 10 weight %, with about 0.2 weight % to about 5 weight % being preferred. The aluminosilicate must have at least 0.1% by weight of Group VIII metal present in the composition in order to maintain catalytic activity for the conversion of methanol in the presence of a hydrogen cofeed to $C_{2-4}$ hydrocarbons.

Representative ion-exchange techniques are disclosed in a wide variety of patents including U.S. Pat. Nos. 3,140,249, 3,140,251 and 3,140,253, which are incorporated herein by reference.

Various metals may be ion-exchanged into the internal structure of the aluminosilicates in accordance with this invention. Group VIII metals are intended to be included in the scope of this invention, with platinum, palladium, ruthenium and palladium-manganese being preferred.

The aluminosilicates that are prepared in accordance with the present invention and used in the conversion of methanol are known in the art. The term aluminosilicate is meant to include synthetically produced and naturally occurring aluminosilicates. The aluminosilicates intended to be included in the scope of this invention include ZSM-5, ZSM-11, ZSM-12, ZSM-34, ZSM-38, mordenite, chabazite, erionite, Zeolon 500 and of which ZSM-5, zeolite Y, mordenite and chabazite are preferred. Zeolon 500 is a commercial product which is a mixture of chabazite and erionite. Zeolite Y, mordenite and chabazite (AW500) are also commercially available.

ZSM-5 is fully disclosed in U.S. Pat. No. 3,702,886, the disclosure of which is herein incorporated by reference.

ZSM-11 is more particularly described in U.S. Pat. No. 3,702,979, the entire contents of which are herein incorporated by reference.

ZSM-12 is more particularly described in U.S. Pat. No. 3,832,449, the entire contents of which are being incorporated by reference.

ZSM-38 is described in U.S. Pat. No. 4,016,859, the entire contents of which are incorporated herein by reference.

Incorporation of a Group VII metal onto the aluminosilicates in accordance with the present invention affects the catalytic activity of the aluminosilicates in the conversion of methanol to low molecular weight hydrocarbons. As is known in the art, small pore aluminosilicates, such as for example, erionite and ZSM-34 give higher $C_{2-3}$ hydrocarbon selectivity than ZSM-5 or Y-zeolites, but rapid coke formation makes them impractical as catalysts.

The aluminosilicates of this invention are exchanged or impregnated with a Group VIII metal and heat treated in air at 540° C. for 4 hours and cooled to ambient temperature. The composition is then subjected to a hydrogen treatment during which the treating temperature is increased from ambient conditions to about 200° C. to about 500° C., preferably about 300° C. to about 500° C. The rate of temperature increase must be controlled. A temperature increase of about 0.1° C. to about 5° C. per minute can be employed with 0.5° C. to about 2.0° C. per minute being preferred. After reaching the desired temperature, the composition is maintained at this temperature for about 0.5 to about 4 hours, preferably about 0.75 hour to about 1.25 hour. The composition is then cooled to ambient temperature in the presence of an inert gas or hydrogen. The treatment of the composition with hydrogen increases the $C_2$–$C_4$ hydrocarbon selectivity when the composition is employed in the conversion of methanol to low molecular weight hydrocarbons in the presence of hydrogen cofeed.

The process for conversion of methanol in the presence of a hydrogen cofeed with an effective amount of the compositions of the present invention, is conveniently conducted at a temperature in the range of about 250° C. to about 500° C., normally 325° C.–500° C., a pressure in the range of about 0 psig (101 kPa) to about 1500 psig (10,442 kPa), preferably 50 psig (446 kPa) to 1000 psig (6995 kPa) in a batch or flow reactor system. The volume ratio of hydrogen to methanol cofeed is conveniently in the range of about 0.5 1 to about 6:1, normally about 3:1. The hydrogen can be diluted with up to 40 volume percent of inert gas (e.g. steam, nitrogen or argon) without affecting catalytic properties.

The process of the present invention is conducted for a time sufficient to form a product mixture containing methane, $C_2$–$C_6$ alkanes and alkenes, carbon dioxide, water and ethers. The product mixture may be entrapped in a suitable trapping means such as a condenser and thereafter separated by standard techniques, e.g. distillation. For example, when utilizing the subject process in a batch-wise fashion, contact times of about 0.1 to about 60, preferably about 0.5 to about 40 minutes are found to be effective. When reacting the subject process continuously, space velocities of about 0.1 to about 20, preferably about 0.5 to about 10 weight hourly space velocity should be utilized.

The activity of the compositions of the present invention is achieved at temperatures of about 325° C.–450° C. Furthermore, the composition deactivates faster at temperatures of about 450° C. to about 500° C. The activity of the composition is decreased at temperatures of about 300° C. to about 325° C. Temperatures in the range of about 325° C. to about 450° C. were preferred for maximizing catalytic activity, service lifetime and selectivity to $C_2$–$C_4$ alkanes.

The process of the present invention can be operated in batch or continuous mode. A continuous flow reactor minimizes secondary reaction of initially formed products and extends the service lifetime of the composition.

It is not known why the crystalline compositions of this invention provide such unexpected properties as high activity for the conversion of methanol in the presence of a hydrogen cofeed to low molecular weight hydrocarbons and the high selectivity for $C_{2-4}$ alkanes. It is possible that the Group VIII metal (e.g. platinum, palladium, ruthenium or palladium-manganese) in the presence of a hydrogen cofeed hydrogenates low molecular weight olefins to saturates before oligomerization can occur.

The following examples are presented as specific embodiments of the present invention and show some of the unique characteristics of the aluminosilicates and are not to be considered as constituting a limitation on the present invention.

EXAMPLE 1

I. Aluminosilicate

A. Ion-Exchange

A 20 gram sample of ammonium zeolite Y aluminosilicate was added to a solution containing 0.6 gram Pd $(NH_3)_4Cl_2$ dissolved in 400 ml deionized water. After being stirred at reflux for 16 hours, the solution was decanted and a second quantity of palladium solution was added and stirred at reflux for 4 hours. After cooling the solid was then washed with deionized water by repeated decantation and was collected by filtration and dried overnight.

B. Catalyst Pretreatment

Before charging Pd-aluminosilicate to a reactor, the preferred pretreatment was to calcine 25 grams of palladium aluminosilicates in air at 540° C. for 4 hours and then cool to ambient temperature. The calcined solid was treated in 5% hydrogen in nitrogen at a temperature program of 1° C./minute to 350° C. and held for 1 hour. After being cooled to ambient temperature in 5% hydrogen, a portion of the composition was charged to the reactor.

EXAMPLE 2-3

Palladium exchanged chabazite (Example 2) and palladium exchanged mordenite (Example 3) were prepared in accordance with the procedure used in Example 1 except that the appropriate aluminosilicate was substituted for zeolite Y.

EXAMPLE 4

This example compares a palladium exchanged Y-zeolite (Pd-Y) and a hydrogen zeolite ($H^+$ — Y) in the conversion of methanol in the presence of a hydrogen cofeed to low molecular weight hydrocarbons. All of the compositions were prepared in accordance with Example 1 and all runs were conducted at 50 psig (446 kPa) in a 316 stainless steel tubular reactor at a weight hourly space velocity of 20.

TABLE I
METHANOL REACTIONS ACTIVITIES OF Pd—Y AND H—Y ZEOLITES $H_2$:$CH_3OH$ FEED

| Ion Form | Pd (1.1 wt. %) | $H^+$ |
|---|---|---|
| HC Yield, %(2) | 35 | 1 |
| HC Sel., %(2) | | |
| $C_1$ | 9 | — |
| $C_2H_4$ | 1 | — |
| $C_2H_6$ | 16 | — |
| $C_3$ | 29 | — |
| $C_4$ | 31 | — |
| $C_{5+}$ | 14 | — |
| Ar | 0 | — |
| Carbon Ratio $C_2 + C_3$ satd./unsatd. | 6.8 | 0 |
| DME Yield, %(2) | 51 | 71 |

(1)Catalyst = 8 wt. % zeolite + 92% $SiO_2$, 18/60 mesh, Temp. = 400° C., Press. = 50 psig, WSHV = 20 ($H_2$:$CH_3OH$ = 2.6 molar ratio). Sampled at 2 hours on stream.
(2)Based on carbon.

The data show that the palladium exchanged Y zeolite has catalytic activity for the conversion of methanol to low molecular weight hydrocarbons. It appears that the hydrogen Y zeolite is not catalytically active for methanol conversion to low molecular weight hydrocarbons, but this is apparently because of rapid deactivation.

EXAMPLE 5

This example compares a palladium exchanged Y zeolite (Pd-Y) and a hydrogen Y-zeolite in the conversion of methanol in the presence of hydrogen and nitrogen cofeed to low molecular weight hydrocarbons. All of the compositions were prepared in accordance with Example 1 and all runs were conducted at 50 psig (446 kPa) in a 316 stainless steel tubular reactor at a weight hourly space velocity of 20.

TABLE II
METHANOL REACTIONS COMPARISON OF HYDROGEN AND NITROGEN COFEEDS(1)

| Catalyst | Pd—Y(2) | | HY |
|---|---|---|---|
| Cofeed | $H_2$ | $N_2$ | $H_2$ |
| HC Yield, %(3) | 52 | 5 | 5 |
| HC Sel., %(3) | | | |
| $C_1$ | 22 | 6 | 15 |
| $C_{2-4}$ | 59 | — | — |
| $C_{5+}$ | 20 | — | — |
| Ar | 0 | — | — |
| DME Yield, %(3) | 0 | 75 | 76 |
| CO Yield, %(3) | 47 | 0 | 0 |

(1)8 wt. % HY zeolite (extrudates) + 92 wt. % $SiO_2$, 18–60 mesh. $Pd^{2+}$ exchange catalyst contains 0.9 wt. % Pd based on zeolite. Reaction temperature 400° C., Press. = 50 psig, 25% $CH_3OH$, 75% cofeed (molar), sampled after 2 hours on stream.
(2)Hydrogen-treated @ 1°/min. to 500° C.
(3)Based on carbon.

The data show that the palladium exchanged Y-zeolite (Pd-Y) in the presence of a hydrogen cofeed is catalytically active for methanol conversion, while the palladium exchanged Y zeolite (Pd-Y) and hydrogen Y zeolite ($H^+$ — Y) that were tested in the presence of a nitrogen and hydrogen cofeed respectively deactivate in less that 2 hours. This shows that hydrogen and Group VIII metals (e.g. palladium) are critical to the present invention.

EXAMPLE 6

This example compares the catalytic activity of palladium exchanged Y zeolites (catalysts 1A, 1B) in the conversion of methanol to low molecular weight hydrocarbons and the effect of hydrogen treatment on the two catalysts. All of the compositions were prepared in accordance with Example 1 and all runs were conducted at 50 psig (446 kPa) in a 316 stainless steel tubular reactor at a weight hourly space velocity of 10. The hydrogen treatment was not subject to careful control.

TABLE III
METHANOL REACTIONS BATCH TO BATCH VARIATIONS OF Pd—Y ZEOLITES(1)

| Catalyst(2) | 1A | 1B |
|---|---|---|
| HC Yield, %(3) | 64 | 39 |
| HC Sel., %(3) | | |
| $C_1$ | 9 | 5 |
| $C_{2-4}$ | 72 | 50 |
| $C_{5+}$ | 19 | 45 |
| Ar. | 0 | 0 |
| DME Yield, %(3) | 5 | 44 |

(1)Catalyst: 8 wt. % zeolite + 92 wt. % $SiO_2$, 18/60 mesh, Temp. = 400° C., Press. = 50 psig, $H_2$/$CH_3OH$ = 2.6, WHSV = 10, AHSV = 500. Zeolite $H_2$ treated at 500° C.
(2)1A = first batch
1B = same batch of Pd—Y as 1A-separate $H_2$ treatment.
(3)Based on carbon.

The data show in compositions 1A and 1B that hydrogen pretreatment affects hydrocarbon yield and $C_{2-4}$ hydrocarbon selectivity. Compositions 1A and 1B were from the same batch, but were hydrogen treated seperately. This demonstrates that a uncontrolled hydrogen treatment gave variable hydrocarbon yield and $C_2$-$C_4$ selectivity.

EXAMPLE 7

This example compares the effects of controlled hydrogen treatment temperatures on palladium exchanged Y zeolites (2 and 3) on $C_{2-4}$ hydrocarbon selectivity in the conversion of methanol in the presence of a hydrogen cofeed to low molecular weight hydrocarbons. All of the compositions were prepared in accordance with Example 1 and all runs were conducted at 50 psig (446 kPa) in a 316 stainless steel tubular reactor at a weight hourly space velocity of 10.

TABLE IV
METHANOL REACTIONS COMPARISON OF HYDROGEN REDUCTION CONDITIONS ON Pd—Y ZEOLITES(1)

| Composition | 2 | 3 |
|---|---|---|
| Hydrogen Treatment, °C.(2) | 350 | 500 |
| HC Yield, %(3) | 50 | 52 |
| HC Sel., %(3) | | |
| $C_1$ | 11 | 22 |
| $C_2-C_4$ | 73 | 59 |
| $C_{5+}$ | 16 | 20 |
| Ar. | 0 | 0 |
| DME Yield, %(3) | 24 | 0 |
| CO Yield, %(3) | 13 | 47 |

(1)Catalyst: 8 wt. % Pd exchanged (0.9 wt. %) HY zeolite (+92 wt. % $SiO_2$, 18–60 mesh, Temp. = 400° C., Press. = 50 psig, 25% $CH_3OH$ 75% $H_2$ cofeed, sampled after 2 hours on stream, WHSV = 10 (based on $CH_3OH$).
(2)Calcined @ 540° C. in air, hydrogen-treatment at 1°/min.
(3)Based on Carbon.

The data show that the temperature of the hydrogen treatment affects $C_2-C_4$ hydrocarbon selectivity. Composition 2 heated at 1°/minute to 350° C. had a better $C_2-C_4$ hydrocarbon selectivity than composition 3 which was heated at 1°/minute to 500° C.

EXAMPLE 8

This example compares the effects of lower hydrogen treatment and calcination temperatures on the selectivity of $C_{2-4}$ hydrocarbons. Compositions 4 and 5 were calcined at 540° C. and 200° C. and hydrogen treated at 350° C. and 200° C. respectively. Compositions 6 and 7 were nitrogen treated at 200° C. and hydrogen treated at 200° C. and 350° C. respectively. All of the compositions were prepared in accordance with Example 1 and all runs were conducted at 50 psig (446 kPa) in a 316 stainless steel tubular reaction at a weight hourly space velocity of about 10.

TABLE V
METHANOL REACTIONS WITH Pd—HY ZEOLITES EFFECTS OF ACTIVATION TEMPERATURE-$H_2$—$CH_3OH$ COFEED(1)

| Run | 4 | 5 | 6 | 7 |
|---|---|---|---|---|
| Calcination Atmosphere | air | air | $N_2$ | $N_2$ |
| Calcination Temp. °C. | 540 | 200 | 200 | 200 |
| $H_2$ Redn. Temp. °C. | 350 | 200 | 200 | 350 |
| HC Yield, %(2) | 61 | 15 | 53 | 20 |
| HC Sel., %(2) | | | | |
| $C_1$ | 8 | 98 | 97 | 97 |
| $C_{2-4}$ | 71 | 0 | 0 | 0 |
| $C_{5+}$ | 21 | 2 | 3 | 0 |
| Ar. | 0 | 0 | 0 | 0 |
| DME Yield, %(2) | 20 | 32 | 5 | 38 |
| CO Yield, %(2) | 6 | 45 | 0 | 34 |
| WHSV | 10.0 | 10.7 | 8.1 | 10.0 |

(1)Catalyst = 8 wt. % Pd exchanged (0.9 wt. %) HY-zeolite + 92 wt. % $SiO_2$, 18–60 mesh, Temp. = 400° C., Press. = 50 psig, 25% $CH_3OH$ - 75% $H_2$ cofeed, sampled after 2 hours on stream
(2)Based on carbon.

The data show that lower air calcination and hydrogen treatment temperature gives poor $C_2-C_4$ hydrocarbon selectivity. (Compare compositions 4 and 5). Compositions 6 and 7 that were heated in nitrogen instead of air at 200° C. also showed poor $C_2-C_4$ hydrocarbon selectivity.

EXAMPLE 9

This example shows that high $C_2-C_4$ hydrocarbon selectivity was obtained when compositions (8, 9 and 10) are hydrogen treated at a temperature rate of 1° C./minute to 350° C. All compositions were prepared seperately in accordance with Example 1 and all runs were conducted at 50 psig in a 316 stainless steel tubular reactor at a weight hourly space velocity of 10.

TABLE VI
METHANOL REACTIONS REPRODUCIBILITY OF $C_{2-4}$ HYDROCARBON SELECTIVITY WITH Pd—Y ZEOLITE(1)

| Run | 8 | 9 | 10 |
|---|---|---|---|
| Hydrogen Treatment °C.(2) | 350 | 350 | 350 |
| HC Yield, %(3) | 61 | 67 | 50 |
| HC Sel., %(3) | | | |
| $C_1$ | 8 | 17 | 11 |
| $C_{2-4}$ | 71 | 74 | 73 |
| $C_{5+}$ | 21 | 9 | 16 |
| Ar. | 0 | 0 | 0 |
| DME Yield, %(3) | 20 | 1 | 24 |
| CO Yield, %(3) | 6 | 20 | 13 |

(1)Catalyst = 8 wt. % Pd exchanged (1–3 wt. %) HY zeolite, powdered extrudates + 92 wt. % $SiO_2$, 18–60 mesh, Temp. = 400° C., Press. = 50 psig, 25% $CH_3OH$ - 75% $H_2$ cofeed, WHSV = 10, sampled after2 hours on steam. All three catalysts are from different Pd exchanges.
(2)Calcined at 540° C. in air, hydrogen treatment at 1°/min.
(3)Based on carbon.

The data show high selectivity for $C_2-C_4$ hydrocarbons when compositions 8, 9 and 10 are heat treated at a 1° C./minute to 350° C.

EXAMPLE 10

This example compares the effect on $C_{2-4}$ hydrocarbon selectivity and hydrocarbons yield when weight hourly space velocity (WHSV) and temperature are changed for hydrogen Y compositions (A and B) and palladium exchanged Y compositions (11, 12, 13 and 14). All of the compositions were prepared in accordance with Example 1 and all runs were conducted at 50 psig (446 kPa) in a 316 stainless steel tubular reactor.

TABLE VII
METHANOL REACTIONS EFFECT OF SPACE VELOCITY AND TEMPERATURE ON THE ACTIVITIES OF H—Y AND Pd—Y ZEOLITES(1)

| | H—Y—Zeolite, Calcn. 540° C. | | 1.1% Pd—Y—Zeolite, Redn. $H_2$, 500° C. | | | |
|---|---|---|---|---|---|---|
| Run | A | B | 11 | 12 | 13 | 14(2) |
| Temp. °C. | 400 | 400 | 350 | 400 | 400 | 450 |
| WHSV | 10 | 20 | 10 | 10 | 20 | 5 |
| $CH_3OH$, mol % | 33.7 | 26.5 | 28.9 | 27.5 | 27.9 | 16.7 |
| HC Yield, %(3) | 5 | 5 | 23 | 64 | 35 | 18 |
| HC Sel., %(3) | | | | | | |
| $C_1$ | — | — | 34 | 9 | 9 | 57 |
| $C_2-C_4$ | — | — | 42 | 72 | 77 | 20 |
| $C_{5+}$ | — | — | 25 | 19 | 14 | 24 |
| Ar | — | — | 0 | 0 | 0 | 0 |
| DME Yield, %(3) | 68 | 71 | 42 | 5 | 46 | 49 |

(1)Catalyst - 8 wt. % zeolite + 92 wt. % $SiO_2$, 18/60 mesh, Conditions - Press. psig = 50, 2 hrs. on stream, Feed-Methanol/Hydrogen.
(2)Catalyst - 25 wt. % zeolite + 75 wt. % $SiO_2$, 18/60 mesh.
(3)Based on carbon.

Comparision of compositions 11 and 12 show that higher $C_{2-4}$ selectivity was obtained at 400° C. Comparison of compositions 12 and 13 show tha WHSV has little effect on $C_{2-4}$ selectivity, but hydrocarbon yield was lower at the higher velocity. Composition 14 which was tested at a high temperature and low space velocity gave poor results. Compositions A and B which are not of the present invention, showed little activity.

EXAMPLE 11

The example compares palladium exchanged ZSM-5 (compositions 15 and 16) with prior art ZSM-5 (composition C) that was not palladium exchanged. All of the compositions are prepared in accordance with Example 1 and all were conducted at 90 psig (723 kPa) in a 316 stainless steel tubular reactor at a weight hourly space velocity of 5.

TABLE VIII

METHANOL REACTIONS
THE EFFECT OF Pd—INCORPORATION METHOD
OF CATALYTIC ACTIVITY AND SELECTIVITY(1,2)

|  | C ZSM-5 | 15 1% Pd Imprg. ZSM-5 | 16 2% Pd Exchg. ZSM-5 |
|---|---|---|---|
| Mol. % $CH_3OH$ | 19.2 | 23.3 | 20.7 |
| Hours on Stream | 27 | 24 | 24 |
| HC Yield, %(3) | 96 | 85 | 84 |
| HC Sel., %(3) | | | |
| $C_1$ | 1 | 3 | 10 |
| $C_2$-$C_4$ | 44 | 63 | 58 |
| $C_{5+}$ | 41 | 34 | 32 |
| Ar | 15 | 0 | 0 |
| AHSV | 4,490 | 3,590 | 3,530 |
| Oxy. Yield, %(3) | 2 | 12 | 16 |
| Oxy. Sel., %(3) | 100 | 39 | 0 |
| DME mMol.$CH_3OH$/hr. | 535 | 528 | 465 |

(1)Temp. = 400° C., Press. = 90 psig, $H_2$ cofeed, WHSV = 5.
(2)50% alumina diluted extrudates.
(3)Based on carbon.

The data showed that in composition 15 and 16 $C_{2-4}$ hydrocarbon selectivity was increased by the addition of palladium over the prior art composition C.

EXAMPLE 12

This example compares the activity and selectivity of ruthenium or palladium impregnated $NH_4^+$/AW500 with palladium exchanged AW500. All compositions were prepared in accordance with Example 1 except that aqueous impregnation rather than ion exchange was employed, and all runs were conducted at 50 psig (446 kPa) in a 316 stainless steel tubular reactor at a weight hourly space velocity of 0.8.

TABLE IX

METHANOL REACTIONS Activity/Selectivity of
Ru or Pd—Impregnated $NH_4$ vs Pd Exchanged AW500(1)

| AW500 Prep. Method | Ru Impregnated | Pd Impregnated | Pd Exchanged |
|---|---|---|---|
| HC Yields %(2) | 24 | 21 | 34 |
| HC Sel., %(2) | | | |
| $C_1$ | 13 | 14 | 25 |
| $C_2$-$C_4$ | 79 | 80 | 66 |
| $C_{5+}$ | 9 | 6 | 10 |
| DME Yield, % | 47 | 54 | 41 |
| CO Yield, % | 7 | 1 | 4 |
| $CO_2$ Yield, % | 0 | 0 | 0 |
| WHSV | 0.8 | 0.7 | 0.8 |

(1)Catalyst: 100 wt. % AW500 chabazite, 18-60 mesh; Impregnated = a palladium or ruthenium salt was concentrated onto the ammonium aluminosilicate surface to give a dry-metal wt. % of 0.2. Exchanged = the metal salt was exchanged with theammonium aluminosilicate to give a dry metal wt. % of 1.9.
Conditions: Temp. 400° C.; Press. 50 psig; Feed 30 mol. % methanol + 70 mol. % $H_2$, sampled after 2 hours on stream.
(2)Based on carbon These data show that for the short term test, the metal impregnated AW500 aluminosilicates were not as active as those with the metal exchanged onto the aluminosilicate, but they are more selective for $C_{2-4}$ hydrocarbon formation.

EXAMPLE 13

This example compares the methanol conversion activities of palladium exchanged mordenite of the present invention and hydrogen mordenite. All compositions were prepared in accordance with Example 1, except that mordenite was substituted for the aluminosilicate. All runs were conducted at 50 psig (446 kPa) in a 316 stainless steel tubular reactor at a weight hourly space velocity of 0.8.

TABLE X

METHANOL REACTIONS
ACTIVITIES OF Pd—AND-H—MORDENITES(1,2)

| Ion Form | $H^+$ | $Pd^{2+}$ (1.3%) |
|---|---|---|
| HC Yield, %(3) | 43 | 97 |
| HC Selectivity, % | | |
| $C_1$ | 13 | 15 |
| $C_2$-$C_4$ | 72 | 71 |
| $C_{5+}$ | 15 | 12 |
| Ar | 0 | 2 |
| DME Yield, %(3) | 23 | 3 |
| CO/$CO_2$ Yield, %(3) | 0 | 1 |
| WHSV | 0.8 | 0.8 |

(1)Catalyst = 100 wt. % zeolite, 18-60 mesh, Temp. = 400° C., Press. = 50 psig, 30 mole % $CH_3OH$, 70 mole % $H_2$, sampled after 2 hours on stream.
(2)Zeolon 900.
(3)Based on carbon.

The data show the increased hydrocarbon yield with a palladium exchanged mordenite (Zeolon 900 mordenite).

EXAMPLE 14

This example compares the methanol conversion activities of palladium exchanged chabazite of the present invention and hydrogen chabazite. All compositions were prepared in accordance with Example 1, except that chabazite was substituted for the aluminosilicate. All runs were conducted at 50 psig. (446 kPa) in a 316 stainless steel tubular reactor at a weight hourly space velocity of 0.7.

TABLE XI

METHANOL REACTIONS
THE EFFECT OF ION FORM ON SELECTIVITY
OF CHABAZITES(1)

| Ion Form(2) | $H^+$ | $Pd^{2+}$ (2.0%) |
|---|---|---|
| HC Yield, %(3) | 12 | 85 |
| HC Sel., %(3) | | |
| $C_1$ | 5 | 15 |
| $C_{2-4}$ | 54 | 83 |
| $C_{5+}$ | 41 | 2 |
| DME Yield, %(3) | 62 | 7 |
| CO Yield, %(3) | 0 | 14 |
| WHSV | 0.7 | 0.7 |

(1)Catalyst = 100% AW500, 18/60 mesh, Temp = 400° C., Press. = 50 psig, 30 mole % $CH_3OH$, 70 mole % $H_2$ sampled after 2 hours on stream.
(2)Prepared by ion exchange.
(3)Based on carbon.

The data show an improved hydrocarbon yield and $C_{2-4}$ selectivity with the palladium exchange chabazite (AW500) when compared to the hydrogen ion chabazite.

EXAMPLE 15

This example compares the methanol conversion activities of palladium exchanged chabazite and palladium manganese exchanged chabazite of the present invention. All compositions were prepared in accordance with Example 1, except that chabazite was substituted for the aluminosilicate. All runs were conducted at 50 psig. (446 kPa) in a 316 stainless steel tubular reactor at a weight hourly space velocity of 0.8.

TABLE XII

METHANOL REACTIONS
EFFECT OF THE ION FORM ON STABILITY/
ACTIVITY/SELECTIVITY OF CHABIZITES(1)

| Ion Form | $Pd^{+2}$ | | $Pd^{+2}-Mn^{+2}$ | |
|---|---|---|---|---|
| Time on stream, hrs. | 2 | 22 | 2 | 22 |
| HC Yield, %(2) | 85 | 24 | 87 | 79 |
| HC Sel., % (2) | | | | |
| $C_1$ | 15 | 43 | 10 | 10 |
| $C_{2-4}$ | 83 | 52 | 87 | 84 |
| $C_{5+}$ | 2 | 5 | 4 | 6 |
| DME Yield, %(2) | 7 | 39 | 0 | 7 |
| CO Yield, % (2) | 14 | 16 | 13 | 13 |

(1)Catalyst = 100 wt. % AW-500 (chabazite), 18-60 mesh; Conditions = Temp. = 400° C., Press. = 50 psig., WHSV = 0.8, 30 mole % $CH_3OH$, 70 mole % $H_2$. All catalysts prepared by ion exchanging $NH_4^+$—AW-500.
(2)Based on carbon.

The data show that the palladium-manganese exchanged chabazite has a higher hydrocarbon yield and better $C_{2-4}$ selectivity after 22 hours on stream when compared to the palladium exchanged chabazite after the same time on stream. However, the palladium-manganese exchanged chabazite and palladium exchanged chabazite have similar hydrocarbon yields and $C_{2-4}$ selectivity when on stream for 2 hours.

Obviously, other modifications and variations of the present invention are possible in the light of the above teachings. It is, therefore, to be understood that changes may be made in the particular embodiments of this invention which are within the full intended scope of the invention as defined by the appended claims.

What is claimed is:

1. A method for the conversion of methanol comprising:
    contacting methanol in the presence of a hydrogen cofeed with a catalytically effective amount of a crystalline aluminosilicate composition under conversion conditions effective to provide $C_2$-$C_4$ hydrocarbons at a selectivity of at least 50%, said conversion conditions comprising a temperature of 325°-500° C. and a pressure of 50-1000 psig and said crystalline aluminosilicate composition being prepared by a method which comprises:
    (a) contacting a crystalline aluminosilicate with a Group VIII metal salt solution to incorporate about 0.2 to about 5% by weight of said metal onto said crystalline aluminosilicate, said Group VIII metal being platinum, palladium or ruthenium and said crystalline aluminosilicate being ZSM-5, zeolite Y, or mordenite;
    (b) calcining the Group VIII metal crystalline aluminosilicate in air at a temperature of about 300° C. to about 600° C. for at least 4 hours;
    (c) heating the calcined Group VIII metal crystalline aluminosilicate in the presence of hydrogen from ambient temperature to an elevated temperature of about 300° C. to about 500° C. at a rate of temperature increase of about 0.5° to about 2.0° C. per minute;
    (d) maintaining said crystalline aluminosilicate at said temperature for about 0.75 to about 1.25 hour; and
    (e) cooling said crystalline aluminosilicate to ambient temperature in the presence of hydrogen.

2. A method according to claim 1, wherein the Group VIII metal is palladium, said Group VIII metal salt being employed in combination with a manganese salt.

3. A method according to claim 1 or 2, wherein the Group VIII metal is ion-exchanged onto the crystalline aluminosilicate.

4. A method according to claim 1 or 2, wherein the Group VIII metal is impregnated onto the crystalline aluminosilicate.

* * * * *